(12) United States Patent
Cavaco Paulo et al.

(10) Patent No.: US 12,329,841 B2
(45) Date of Patent: Jun. 17, 2025

(54) ODORANT-BINDING PROTEIN COMPOSITIONS, METHODS AND USES THEREOF

(71) Applicant: Universidade do Minho, Braga (PT)

(72) Inventors: Artur Manuel Cavaco Paulo, Braga (PT); Filipa Daniela Gomes Gonçalves, Braga (PT); Artur Jorge Araújo Magalhães Ribeiro, Braga (PT); Carla Manuela Pereira Marinho Da Silva, Guimaraes (PT)

(73) Assignee: UNIVERSIDADE DO MINHO, Braga (PT)

( * ) Notice: Subject to any disclaimer, the term of this patent is extended or adjusted under 35 U.S.C. 154(b) by 0 days.

(21) Appl. No.: 18/520,428

(22) Filed: Nov. 27, 2023

(65) Prior Publication Data

US 2024/0115481 A1 Apr. 11, 2024

Related U.S. Application Data

(63) Continuation of application No. 18/003,127, filed as application No. PCT/IB2021/056011 on Jul. 5, 2021.

(30) Foreign Application Priority Data

Jul. 3, 2020 (PT) .......................................... 116561
Nov. 6, 2020 (EP) ..................................... 20206292

(51) Int. Cl.
*A61K 8/64* (2006.01)
*A61G 5/12* (2006.01)
*A61K 8/11* (2006.01)
*A61Q 5/00* (2006.01)
*A61Q 5/02* (2006.01)
*A61Q 5/04* (2006.01)
*A61Q 5/06* (2006.01)
*A61Q 5/08* (2006.01)
*A61Q 5/10* (2006.01)
*A61Q 15/00* (2006.01)

(52) U.S. Cl.
CPC .................. *A61K 8/64* (2013.01); *A61K 8/11* (2013.01); *A61Q 15/00* (2013.01)

(58) Field of Classification Search
CPC . A61K 8/64; A61K 8/11; A61Q 15/00; A61Q 5/00; A61Q 5/02; A61Q 5/002; A61Q 5/004; A61Q 5/006; A61Q 5/008; A61Q 5/04; A61Q 5/06; A61Q 5/065; A61Q 5/08; A61Q 5/10; A61Q 5/12
See application file for complete search history.

(56) References Cited

U.S. PATENT DOCUMENTS

| | | |
|---|---|---|
| 5,028,419 A | 7/1991 | Pigiet |
| 5,635,170 A | 6/1997 | Lang et al. |
| 6,020,163 A | 2/2000 | Conklin |
| 7,622,273 B2 | 11/2009 | Gibbs |
| 7,919,456 B2 | 4/2011 | Ghosh |
| 8,034,338 B2 | 10/2011 | Loibner et al. |
| 8,383,580 B2 * | 2/2013 | Rui ..................... A61K 38/17 514/21.3 |
| 8,809,259 B2 * | 8/2014 | Berry ..................... A23L 33/18 514/4.9 |
| 9,713,604 B2 | 7/2017 | Dreher |
| 10,709,655 B2 | 7/2020 | Cavaco et al. |
| 11,642,298 B2 | 5/2023 | Cavaco Paulo et al. |
| 11,712,410 B2 | 8/2023 | Sahib et al. |
| 12,102,706 B2 | 10/2024 | Cavaco Paulo et al. |
| 12,115,242 B2 | 10/2024 | Cavaco Paulo et al. |
| 2006/0272103 A1 | 12/2006 | Barbarat |
| 2006/0286655 A1 | 12/2006 | Philippe |
| 2008/0107614 A1 | 5/2008 | Fahnestock et al. |
| 2010/0015070 A1 | 1/2010 | Bollschweiler et al. |
| 2010/0272666 A1 | 10/2010 | Breakspear et al. |
| 2012/0087862 A1 | 4/2012 | Hood et al. |
| 2013/0059772 A1 | 3/2013 | Kumar |
| 2013/0224269 A1 | 8/2013 | Khan et al. |
| 2016/0271043 A1 | 9/2016 | Cavaco Paulo et al. |
| 2020/0121581 A1 | 4/2020 | Shoseyov et al. |
| 2021/0393500 A1 | 12/2021 | Cavaco Paulo et al. |
| 2022/0151977 A1 * | 5/2022 | Stamps ................ C12N 15/70 |
| 2022/0287944 A1 | 9/2022 | Costache et al. |
| 2023/0248627 A1 | 8/2023 | Cavaco et al. |
| 2023/0248631 A1 | 8/2023 | Cavaco Paulo et al. |
| 2023/0301894 A1 | 9/2023 | Cavaco Paulo et al. |

(Continued)

FOREIGN PATENT DOCUMENTS

| | | |
|---|---|---|
| CN | 103126949 A | 6/2013 |
| CN | 104940071 A | 9/2015 |

(Continued)

OTHER PUBLICATIONS

Yampolsky et al., "The Exchangeability of Amino Acids in Proteins," Genetics, 2005, 170: 1459-1472. (Year: 2005).*
Rudinger, J., "Characteristics of the amino acids as components of a peptide hormone sequence," Peptide Hormones, J.A, Parsons , MA, BM, BCh, Jun. 1976, pp. 1-7. (Year: 1976).*
Berendsen, HJC, "A Glimpse of the Holy Grail?" Science, 1998, 282: 642-643. (Year: 1998).*
Ngo et al., "Computational Complexity, Protein Structure Prediction, and the Levinthal Paradox," The Protein Folding Problem and Tertiary Structure Prediction, K. Merc, Jr. and S. Le Grand Editors, 1994, 491-495. (Year: 1994).*

(Continued)

*Primary Examiner* — Julie Ha
(74) *Attorney, Agent, or Firm* — Leason Ellis LLP

(57) ABSTRACT

A composition comprising an odorant-binding protein for use in applications, e.g., cosmetic applications, such as for skin or hair care is described. A composition comprising an odorant-binding protein and an active agent, wherein the active agent is released when in presence of an electrolyte solution is described. A kit and an article comprising the composition comprising an odorant-binding protein are also encompassed.

17 Claims, 1 Drawing Sheet

Specification includes a Sequence Listing.

(56) References Cited

U.S. PATENT DOCUMENTS

| | | |
|---|---|---|
| 2023/0338263 A1 | 10/2023 | Cavaco Paulo et al. |
| 2023/0355499 A1 | 11/2023 | Sahib et al. |
| 2023/0414478 A1 | 12/2023 | Cavaco Paulo et al. |
| 2023/0414479 A1 | 12/2023 | Cavaco Paulo et al. |
| 2023/0415070 A1 | 12/2023 | Cavaco Paulo et al. |
| 2024/0082135 A1 | 3/2024 | Cavaco Paulo et al. |
| 2024/0108560 A1 | 4/2024 | Staley et al. |
| 2024/0316187 A1* | 9/2024 | Von Mutius ............ A61P 37/08 |

FOREIGN PATENT DOCUMENTS

| | | |
|---|---|---|
| EP | 0335654 A2 | 10/1989 |
| EP | 0488242 A1 | 6/1992 |
| EP | 1238645 A2 | 9/2002 |
| EP | 1705188 A1 | 9/2006 |
| FR | 2706300 A1 | 12/1994 |
| FR | 2876286 A1 | 4/2006 |
| GB | 103484 A | 1/1918 |
| JP | H0656889 A | 3/1994 |
| JP | H1112138 A | 1/1999 |
| JP | 2005151849 A | 6/2005 |
| PT | 103484 A | 11/2007 |
| WO | WO-9711672 A1 | 4/1997 |
| WO | WO-0023039 A2 | 4/2000 |
| WO | WO-0051556 A1 | 9/2000 |
| WO | WO-0064405 A2 | 11/2000 |
| WO | WO-0112806 A2 | 2/2001 |
| WO | WO-0123890 A1 | 4/2001 |
| WO | WO-2004048399 A2 | 6/2004 |
| WO | WO-2005049834 A1 | 6/2005 |
| WO | WO-2006001536 A1 | 1/2006 |
| WO | WO-2007136286 A1 | 11/2007 |
| WO | WO-2008081348 A2 | 7/2008 |
| WO | WO-2010010145 A1 | 1/2010 |
| WO | WO-2011072991 A1 | 6/2011 |
| WO | WO-2012013593 A1 | 2/2012 |
| WO | WO-2015056216 A2 | 4/2015 |
| WO | WO-2020181395 A1 | 9/2020 |
| WO | WO-2023081711 A1 | 5/2023 |
| WO | WO-2024073683 A2 | 4/2024 |
| WO | WO-2024206473 A1 | 10/2024 |

OTHER PUBLICATIONS

Schinzel et al., "The phosphate recognition site of *Escherichia coli* Maltodextrin phosphorylase," 1991, 286 (1,2): 125-128. (Year: 1991).*

Sigma, "Designing Custom Peptides," pp. 1-2. Accessed Dec. 6, 2004. (Year: 2004).*

Voet et Voet, Biochemistry, Second Edition, John Wiley & Sons, Inc., pp. 235-241. (Year: 1995).*

Bradley et al., "Limits of Cooperativity in a Structurally Modula Protein: Response of the Notch Ankyrin Domain to Analogous Alanine Substitutions in Each Repeat," J. Mol. Biol., 2002, 324: 373-386. (Year: 2002).*

Blast glossary downloaded from www.ncbi.nlm.nih.gov on May 2, 2020.

Blast search for SEQ ID No. 1, downloaded May 2, 2020 (2020).

Blast search for SEQ ID No. 2, downloaded May 2, 2020 (2020).

Co-pending U.S. Appl. No. 18/252,712, inventors Cavaco; Paulo Artur Manuel et al., filed May 11, 2023.

Co-pending U.S. Appl. No. 18/339,889, inventors Cavaco; Paulo Artur Manuel et al., filed Jun. 22, 2023.

Co-pending U.S. Appl. No. 18/339,927, inventors Cavaco; Paulo Artur Manuel et al., filed Jun. 22, 2023.

Co-pending U.S. Appl. No. 18/478,320, inventors Staley; Karis et al., filed Sep. 29, 2023.

Co-pending U.S. Appl. No. 18/497,900, inventors Cavaco Paulo; Arthur Manuel et al., filed Oct. 30, 2023.

Dow, Carbowax Sentry Polyethylene Glycols, published online 2011.

Fernanda Reis Gavazzoni Dias. Hair Cosmetics: An Overview. International Journal of Trichology 7:2-15 (2015).

Fernandes et al. Keratin-based peptide: biological evaluation and strengthening properties on relaxed hair. International Journal of Cosmetic Science 34(4):338-346 (2012).

Koonin et al. Chapter 2 Evolutionary Concept in Genetics and Genomics. MY. Sequence—Evolution—Function: Computational Approaches in Comparative Genomics. Boston: Kluwer Academic. Available from: https:// www.ncbi.nlnn.nih.gov/books/NBK20260/ (pp. 3 ) (2003).

Marabotti et al. The misuse of terms in scientific literature. Bioinformatics 26(19):2498 (2010).

Naturally Curly, http://www.naturallycurly.com/curlreading/kinky-hair-type-4a/ingredients-commonly-used-in-hair-care-productspeg-modified-materials/, published online Jun. 8, 2010.

PCT/IB2014/065375 International Search Report and Written Opinion dated Jun. 7, 2015.

Romanowski. An introduction to cosmetic technology. American Oil Chemists' Society. Available at https://www.aocs.org/stay-informed/inform-magazine/featured-articles/an-introduction-to-cosmetic-technology-april-2015?SSO=True (8 pgs.) (2015).

Shimomura et al. Human Hair Keratin-Associated Proteins. J Investig Dermatol Symp Proc 10:230-233 (2005).

Thesis from Celia Freitas Da Cruz, Unraveling and modulating human hair morphology features (192 pgs) (2012).

Uniprot Protein Database, protein accession A8MUXO , Keratin-associated protein 16-1, accessed on Dec. 18, 2019.

Uniprot Protein Database, protein accession P26371 , Keratin-associated protein 5-9, accessed on Dec. 18, 2019.

Uniprot Protein Database, protein accession Q9NSB0, Type II hair keratin 6, accessed on Dec. 18, 2019.

Uniprot Protein Database, protein Accession Q9NSB5, accessed on Nov. 8, 2019.

Uniprot protein database, protein Type II hair keratin 1, protein accession Q9NSB5, accessed on Aug. 28, 2017.

U.S. Forest Service entry on soaps at www.fs.fed.US/wildflowers/ ethnobotany/soaps.shtra, downloaded Sep. 29, 2020 (2020).

U.S. Appl. No. 15/030,313 Office Action dated Aug. 29, 2018.
U.S. Appl. No. 15/030,313 Office Action dated Aug. 31, 2017.
U.S. Appl. No. 15/030,313 Office Action dated Jan. 11, 2019.
U.S. Appl. No. 15/030,313 Office Action dated Jan. 24, 2018.
U.S. Appl. No. 15/030,313 Office Action dated Jul. 18, 2019.
U.S. Appl. No. 15/030,313 Office Action dated Mar. 2, 2017.
U.S. Appl. No. 16/122,796 Office Action dated Apr. 15, 2021.
U.S. Appl. No. 16/122,796 Office Action dated Apr. 28, 2023.
U.S. Appl. No. 16/122,796 Office Action dated Jan. 5, 2023.
U.S. Appl. No. 16/122,796 Office Action dated May 4, 2020.
U.S. Appl. No. 16/122,796 Office Action dated Oct. 1, 2020.
U.S. Appl. No. 16/122,796 Office Action dated Sep. 20, 2022.
U.S. Appl. No. 16/439,889 Office Action dated Apr. 1, 2022.
U.S. Appl. No. 16/439,889 Office Action dated Jan. 3, 2020.
U.S. Appl. No. 16/439,889 Office Action dated Sep. 15, 2022.
U.S. Appl. No. 18/164,515 Office Action dated Oct. 12, 2023.
U.S. Appl. No. 18/334,287 Office Action dated Oct. 10, 2023.

Yang. Chapter 36: Hair Care Cosmetics. Cosmetic Science and Technology: Theoretical Principles and Applications (pp. 601-615) (2017).

Castro et al. The Structural Properties of Odorants Modulate Their Association to Human Odorant Binding Protein. Biomolecules 11(2):145 (2021).

CN104940071A English Translation Published: Sep. 30, 2015.

EP1238645A2 English Translation Published: Sep. 11, 2002.

U.S. Appl. No. 18/339,927 Office Action dated May 8, 2024.

Altschul, Stephen F. et al. Basic Local Alignment Search Tool. Journal of Molecular Biology 215(3):403-410 (1990).

Archunan. Odorant Binding Proteins: a key player in the sense of smell. Bioinformation 14(1):36-37 (2018).

Bignetti et al. Purification and characterisation of an odorant-binding protein from cow nasal tissue. Eur. J. Biochem. 149:227-231 (1985).

Bignetti et al. The pyrazine-binding protein and olfaction. Comp. Biochem. Physiol., 90(1): 1-5 (1988).

(56) References Cited

OTHER PUBLICATIONS

Breer. Olfactory receptors: molecular basis for recognition and discrimination of odors. Anal Bioanal Chem 377(3):427-33 (2003).
Briand et al. Evidence of an Odorant-Binding Protein in the Human Olfactory Mucus: Location, Structural Characterization, and Odorant-Binding Properties. Biochemistry 41:7241-7252 (2002).
Campanella et al., MatGAT: An application that generates similarity/identity matrices using protein or DNA sequences. BMC Bioinformatics 4:29 (2003).
Capo et al. The porcine odorant-binding protein as molecular probe for benzene detection. PloS One 13(9):e0202630 (2018).
Cave et al. Progress in the development of olfactory-based bioelectronic chemosensors. Biosens Bioelectron 123:211-222 (2019).
Cennamo et al. Easy to Use Plastic Optical Fiber-Based Biosensor for Detection of Butanal. PloS One 10(3):e0116770 (2015).
Dal Monte et al. Purification and characterization of two odorant-binding proteins from nasal tisue of rabbit and pig. Comp Biochem Physiol 99(2):445-451 (1991).
Di Pietrantonio et al. Detection of odorant molecules via surface acoustic wave biosensor array based on odorant-binding proteins. Biosens Bioelectron 41:328-34 (2013).
Flower. Beyond the superfamily: the lipocalin receptors. Biochim Biophys Acta 1482:327-336 (2000).
Flower. The lipocalin protein family : structure and function. Biochem. J. 318(Pt 1)(Pt 1): 1-14 (1996).
Garibotti et al. Three Odorant-binding Proteins from Rabbit Nasal Mucosa. Chem Senses 22(4):383-390 (1997).
Goncalves et al. OBP fused with cell-penetrating peptides promotes liposomal transduction. Colloids Surf B Biointerfaces 161:645-653 (2018).
Goncalves et al. Release of Fragrances from Cotton Functionalized with Carbohydrate- Binding Module Proteins. ACS Applied Mater Interfaces 11(31):28499-28506 (2019).
Goncalves et al. Two Engineered OBPs with opposite temperature-dependent affinities towards 1-aminoanthracene. Sci Rep 8 (1):14844 (2018).
Gongalves et al. 1-Aminoanthracene Transduction into Liposomes Driven by Odorant- Binding Protein Proximity. ACS Applied Mater Interfaces 10(32):27531-27539 (2018).
Han et al. Operating Mechanism and Molecular Dynamics of Pheromone-Binding Protein ASP1 as Influenced by pH. PLoS One 9(10):e110565 (2014).
Kozlowski. IPC—Isoelectric Point Calculator. Biol Direct 11(1):55 (2016).
Lazar et al. Molecular and Functional Characterization of an Odorant Binding Protein of the Asian Elephant, Elephas maximus: Implications for the Role of Lipocalins in Mammalian Olfaction. Biochemistry 41:11786-11794 (2002).
Lobel et al. Odorant of different chemical classes interact with distinct odorant binding protein subtypes. Chem Senses 27:39-44 (2002).
Malpeli et al. Chapter 9: Purification and Fluorescent Titration of Cellular Retinol-Binding Protein. In Methods in Molecular Biology; Redfern, C. P. F., Ed .; pp. 111-122 (1998).
Mazzini et al. Dissociation and unfolding of bovine odorant binding protein at acidic pH. J Struct Biol 159(1):82-91 (2007).
Mulla et al. Capacitance-modulated transistor detects odorant binding protein chiral interactions. Nature Commun 6:6010 (2015).
Needleman, Saul B, and Christian D Wunsch. A General Method Applicable to the Search for Similarities in the Amino Acid Sequence of Two Proteins. Journal of Molecular Biology 48(3):443-453 (1970).
Nogueira et al. Peptide anchor for folate-targeted liposomal delivery. Biomacromolecules 16(9):2904-2910 (2015).
Ozeki et al. A study of the suppression of body odour in elderly subjects by anti-fungal agents. Int J Cosmet Sci 38(3):312-8 (2016).
Paolini et al. Porcine odorant-binding protein: structural stability and ligand affinities measured by Fourier-transform infrared spectroscopy and fluorescence spectroscopy. Biochim Biophys Acta 1431:179-188 (1999).
Parisi et al. Unfolding and refolding of porcine odorant binding protein in guanidinium hydrochloride: equilibrium studies at neutral pH. Biochim Biophys Acta 652(2):115-125 (2003).
PCT/IB2021/056011 International Search Report and Written Opinion dated Oct. 6, 2021.
PCT/US2024/021721 International Search Report and Written Opinion dated Jul. 11, 2024.
Pelosi et al. Odorant-Binding Proteins as Sensing Elements for Odour Monitoring. Sensors (Basel) 18(10):3248 (2018).
Pelosi et al. Structure and biotechnological applications of odorant-binding proteins. Appl Microbiol Biotechnol 98(1):61-70 (2014).
Pelosi Odorant-Binding Proteins: Structural Aspects. In Annals New York academy of sciences; Olfaction and Taste XII: an international symposium, pp. 281-293 (1998).
Perduca et al. Crystal Structure of a Truncated Form of Porcine Odorant-Binding Protein. Proteins 42:201-209 (2001).
Pes et al. Isolation of two odorant-binding proteins from mouse nasal tissue. Comp. Biochem. Physiol. 103 (4):1011-1017 (1992).
Pevsner et al. Odorant-binding protein: characterization of ligand binding. J Biol Chem 265(11):6118-6125 (1990).
Sankaran et al. Biology and applications of olfactory sensing system: A review. Sensors and Actuators B: Chemical 171-172:1-17 (2012).
Silva et al. Odorant binding proteins: a biotechnological tool for odour control. Appl Microbiol Biotechnol 98(8):3629-3638 (2014).
Sorokowska et al. Does Personality Smell? Accuracy of Personality Assessments Based on Body Odour. European Journal of Personality 26(5):496-503 (2012).
Spinelli et al. The Structure of the Monomeric Porcine Odorant Binding Protein Sheds Light on the Domain Swapping Mechanism. Biochemistry 37:7913-7918 (1998).
Tegoni et al. Mammalian odorant binding proteins. Biochim Biophys Acta 1482:229-240 (2000).
U.S. Appl. No. 18/003,127 Office Action dated Nov. 14, 2024.

\* cited by examiner

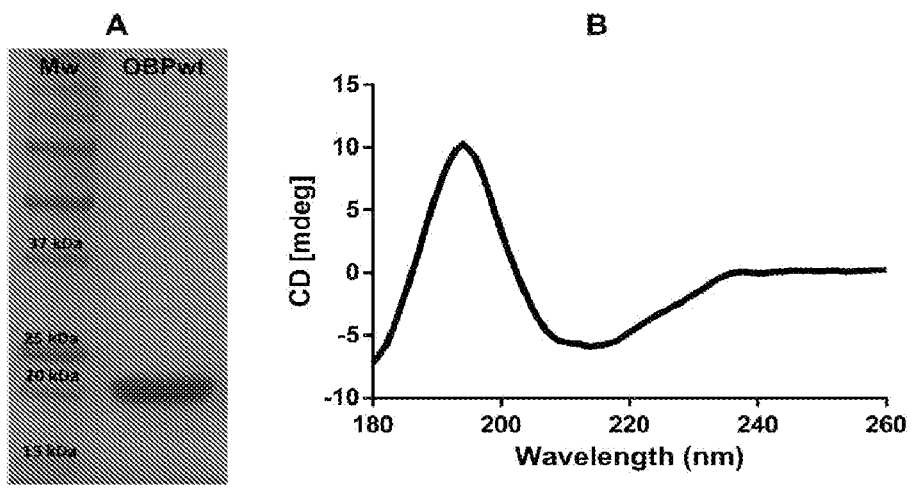

SEQUENCE LISTING

```
Sequence total quantity: 22
SEQ ID NO: 1            moltype = AA  length = 157
FEATURE                 Location/Qualifiers
REGION                  1..157
                        note = Pig OBP (PDB ID 1DZK)
source                  1..157
```

```
                            mol_type = protein
                            organism = Sus scrofa
SEQUENCE: 1
QEPQPEQDPF ELSGKWITSY IGSSDLEKIG ENAPFQVFMR SIEFDDKESK VYLNFFSKEN   60
GICEEFSLIG TKQEGNTYDV NYAGNNKFVV SYASETALII SNINVDEEGD KTIMTGLLGK  120
GTDIEDQDLE KFKEVTRENG IPEENIVNII ERDDCPA                           157

SEQ ID NO: 2            moltype = AA  length = 170
FEATURE                 Location/Qualifiers
REGION                  1..170
                        note = Human OBPIIa (UniProt ID Q9NY56)
source                  1..170
                        mol_type = protein
                        organism = Homo sapiens
SEQUENCE: 2
MKTLFLGVTL GLAAALSFTL EEEDITGTWY VKAMVVDKDF PEDRRPRKVS PVKVTALGGG   60
NLEATFTFMR EDRCIQKKIL MRKTEEPGKF SAYGGRKLIY LQELPGTDDY VFYCKDQRRG  120
GLRYMGKLVG RNPNTNLEAL EEFKKLVQHK GLSEEDIFMP LQTGSCVLEH             170

SEQ ID NO: 3            moltype = AA  length = 170
FEATURE                 Location/Qualifiers
REGION                  1..170
                        note = Human OBPIIb (UniProt ID Q9NPH6)
source                  1..170
                        mol_type = protein
                        organism = Homo sapiens
SEQUENCE: 3
MKTLFLGVTL GLAAALSFTL EEEDITGTWY VKAMVVDKDF PEDRRPRKVS PVKVTALGGG   60
KLEATFTFMR EDRCIQKKIL MRKTEEPGKY SAYGGRKLMY LQELPRRDHY IFYCKDQHHG  120
GLLHMGKLVG RNSDTNREAL EEFKKLVQRK GLSEEDIFTP LQTGSCVPEH             170

SEQ ID NO: 4            moltype = AA  length = 163
FEATURE                 Location/Qualifiers
REGION                  1..163
                        note = Mouse OBP (UniProt ID OBP1A)
source                  1..163
                        mol_type = protein
                        organism = Mus musculus
SEQUENCE: 4
MAKFLLLALT FGLAHAAMEG PWKTVAIAAD RVDKIERGGE LRIYCRSLTC EKECKEMKVT   60
FYVNENGQCS LTTITGYLQE DGKTYKTQFQ GNNRYKLVDE SPENLTFYSE NVDRADRKTK  120
LLFILGHGPL TSEQKEKFAE LAEEKGIPAG NIREVLITDY CPE                    163

SEQ ID NO: 5            moltype = AA  length = 176
FEATURE                 Location/Qualifiers
REGION                  1..176
                        note = Mouse OBP2A (UniProt ID Q8K1H9)
source                  1..176
                        mol_type = protein
                        organism = Mus musculus
SEQUENCE: 5
MKSLLLTILL LGLVAVLKAQ EAPPDDLVDY SGIWYAKAMV HNGTLPSHKI PSIVFPVRII   60
ALEEGDLETT VVFWNNGHCR EFKFVMKKTE EPGKYTAPHN TKVIHVEKTS VNEHYIFYCE  120
GRHNGTSSFG MGKLMGRDSG ENPEAMEEFK NFIKRMNLRL ENMFVPEIGD KCVESD      176

SEQ ID NO: 6            moltype = AA  length = 171
FEATURE                 Location/Qualifiers
REGION                  1..171
                        note = Mouse OBP1B (UniProt ID A2AEP0)
source                  1..171
                        mol_type = protein
                        organism = Mus musculus
SEQUENCE: 6
MMVKFLLLAL VFGLAHVHAH DHPELQGQWK TTAIMADNID KIETSGPLEL FVREITCDEG   60
CQKMKVTFYV KQNGQCSLTT VTGYKQEDGK TFKNQYEGEN NYKLLKATSE NLVFYDENVD  120
RASRKTKLLY ILGKGEALTH EQKERLTELA TQKGIPAGNL RELAHEDTCP E           171

SEQ ID NO: 7            moltype = AA  length = 157
FEATURE                 Location/Qualifiers
REGION                  1..157
                        note = Rat OBP (PDB ID 3FIQ)
source                  1..157
                        mol_type = protein
                        organism = Rattus rattus
SEQUENCE: 7
HHENLDISPS EVNGDWRTLY IVADNVEKVA EGGSLRAYFQ HMECGDECQE LKIIFNVKLD   60
SECQTHTVVG QKHEDGRYTT DYSGRNYFHV LKKTDDIIFF HNVNVDESGK ETNVILVAGK  120
REDLNKAQKQ ELRKLAEEYN IPNENTQHLV PTDTCNQ                           157
```

```
SEQ ID NO: 8                moltype = AA   length = 173
FEATURE                     Location/Qualifiers
REGION                      1..173
                            note = Rat OBP (PDB ID 3ZQ3)
source                      1..173
                            mol_type = protein
                            organism = Rattus rattus
SEQUENCE: 8
MRGSHHHHHH TDPEEASFER GNLDVDKLNG DWFSIVVASD KREKIEENGS MRVFVQHIDV    60
LENSLGFTFR IKENGVCTEF SLVADKTAKD GEYFVEYDGE NTFTILKTDY DNYVMFHLVN   120
VNNGETFQLM ELYGRTKDLS SDIKEKFAKL CVAHGITRDN IIDLTKTDRC LQA          173

SEQ ID NO: 9                moltype = AA   length = 172
FEATURE                     Location/Qualifiers
REGION                      1..172
                            note = Rat OBP (UniProt ID P08937)
source                      1..172
                            mol_type = protein
                            organism = Rattus rattus
SEQUENCE: 9
MVKFLLIVLA LGVSCAHHEN LDISPSEVNG DWRTLYIVAD NVEKVAEGGS LRAYFQHMEC    60
GDECQELKII FNVKLDSECQ THTVVGQKHE DGRYTTDYSG RNYFHVLKKT DDIIFFHNVN   120
VDESGRRQCD LVAGKREDLN KAQKQELRKL AEEYNIPNEN TQHLVPTDTC NQ           172

SEQ ID NO: 10               moltype = AA   length = 159
FEATURE                     Location/Qualifiers
REGION                      1..159
                            note = Bovine OBP (PDB ID 1OBP)
source                      1..159
                            mol_type = protein
                            organism = Bos gaurus
SEQUENCE: 10
AQEEEAEQNL SELSGPWRTV YIGSTNPEKI QENGPFRTYF RELVFDDEKG TVDFYFSVKR    60
DGKWKNVHVK ATKQDDGTYV ADYEGQNVFK IVSLSRTHLV AHNINVDKHG QTTELTGLFV   120
KLNVEDEDLE KFWKLTEDKG IDKKNVVNFL ENEDHPHPE                          159

SEQ ID NO: 11               moltype = AA   length = 175
FEATURE                     Location/Qualifiers
REGION                      1..175
                            note = Boar OBP (PDB ID 1GM6)
source                      1..175
                            mol_type = protein
                            organism = Sus scrofa
SEQUENCE: 11
HKEAGQDVVT SNFDASKIAG EWYSILLASD AKENIEENGS MRVFVEHIRV LDNSSLAFKF    60
QRKVNGECTD FYAVCDKVGD GVYTVAYYGE NKFRLLEVNY SDYVILHLVD VNGDKTFQLM   120
EFYGRKPDVE PKLKDKFVEI CQQYGIIKEN IIDLTKIDRC FQLRGSGGVQ ESSAE        175

SEQ ID NO: 12               moltype = AA   length = 168
FEATURE                     Location/Qualifiers
REGION                      1..168
                            note = Panda OBP (PDB ID 5NGH)
source                      1..168
                            mol_type = protein
                            organism = Ailuropoda melanoleuca
SEQUENCE: 12
HEEGNDVRRN FDVSKISGYW YSVLLASDVR EKTEENSSMR VFVNHIEVLS NSSLLFNMHI    60
KVDGKCTEIA LVSDKTEKDG EYSVEYDGYN VFRIVETDYT DYIIFHLVNF KEKDSFQMME   120
LSAREPDTSE EVRKRFVEYC QKHGIVKENI FDLTEVDRCL QARGSEKA                168

SEQ ID NO: 13               moltype = AA   length = 173
FEATURE                     Location/Qualifiers
REGION                      1..173
                            note = Chinese hamster OBP (Ensembl ID ENSCGRP00015014591.1)
source                      1..173
                            mol_type = protein
                            organism = Cricetulus griseus
SEQUENCE: 13
MVKFLLLAFA LSVSCAHHKI PEISPSEVDG KWRTLYIGAD NTEKVIQGGP LRAYFRHMEC    60
SDECQTLTIT FNTKEEGKCQ THTVVGRKDE DGQYKTGFSG NNDFHVVEKA DGIIIFHNVN   120
VDSSGKKTNV ILVAGKGKSL SKEQKERLEN IAKEFDISKE NIQHLVPTDT CDQ          173

SEQ ID NO: 14               moltype = AA   length = 173
FEATURE                     Location/Qualifiers
REGION                      1..173
                            note = Meishan pig OBP (Ensembl ID ENSSSCP00040041163.1)
source                      1..173
                            mol_type = protein
                            organism = Sus scrofa
```

```
SEQUENCE: 14
MKSLLLSLVL GLVCAQEPQP EQDPFVLSGK WITSYIGSSD LEKIGENAPF QVFMRSIEFD    60
DKESKVYLNF FSKENGICEE FSLIGTKQEG NTYDVNYAGN NKFVVSYASE TALIISNINV   120
DEEGDKTIMT GLLGKGTDIE DQDLEKFKEV TRENGIPEEN IVNIIERDDC PAK          173

SEQ ID NO: 15           moltype = AA   length = 175
FEATURE                 Location/Qualifiers
REGION                  1..175
                        note = Horse OBP (Ensembl ID ENSECAP00000000103.2)
source                  1..175
                        mol_type = protein
                        organism = Equus caballus
SEQUENCE: 15
MQILLLSLVL GVVCAVQEPQ SETDYSLFSG EWNTIYIGSS NIEKISENGP FRILLRRLDL    60
DSAGDRIIYT FFLKVNGQCT KISSLAIKTE ENTYVCHYAG KNKFEILHLS KTAIIIDIVN   120
EDEGGLVTKM VALVGMLGDI QKEDIEKFKE VAKEKEIPEE NIVNIINIDD CPTSE         175

SEQ ID NO: 16           moltype = AA   length = 170
FEATURE                 Location/Qualifiers
REGION                  1..170
                        note = Guinea pig OBP ((Ensembl ID ENSCPOP00000016393.2)
source                  1..170
                        mol_type = protein
                        organism = Cavia porcellus
SEQUENCE: 16
MQILLLALTI GLAYAHQTLD PSEINGQWHT ISIAADNVEK IGEGGPLRGY FHNLHCYDGC    60
KNIGLTFYVK LDGNCQRFDV LGAKQEDSDV YVAQYSGTNH FEVIGKKEDA IAFYNHNTDE   120
TGKETKMIVV VARRDSLTEE EQQKLQEVAG EKGIPKDNIR YFRERDTCAQ               170

SEQ ID NO: 17           moltype = AA   length = 174
FEATURE                 Location/Qualifiers
REGION                  1..174
                        note = Dog OBP ((Ensembl ID ENSCAFP00040020992.1)
source                  1..174
                        mol_type = protein
                        organism = Canis lupus
SEQUENCE: 17
MKILLLCLIL VLACDAHLPL PNVLTQVSGP WKTLYVSSNN LDKIAENGPF RIYIRRINVD    60
IPRLKILFSF FVKVDGECVE KSVEASIGQD NLINAHYAGG NYHQILDVTP NALIGYIVNV   120
DDKGRITKLA SLVGRGAHVN EEDIAKFKKL SREKGIPEEN IIYLGDTDNC PNHE          174

SEQ ID NO: 18           moltype = AA   length = 173
FEATURE                 Location/Qualifiers
REGION                  1..173
                        note = Tibetan pig OBP (Ensembl ID ENSSSCP00015013912.1)
source                  1..173
                        mol_type = protein
                        organism = Sus scrofa
SEQUENCE: 18
MKSLLLSLVL GLVCAQEPQP EQDPFELSGK WITSYIGSSD LEKIGENAPF QVFMRSIEFD    60
DKESKVYLNF FSKENGICEE FSLTGTKQEG NTYDVNYAGN NKFVVSYASE TALIIANINV   120
DEEGDKTIMT GLLGKGTDIE DQDLEKFKEV TRENGIPEEN IVNIIERDDC PAK           173

SEQ ID NO: 19           moltype = AA   length = 314
FEATURE                 Location/Qualifiers
REGION                  1..314
                        note = Cat felis OBP (Ensembl ID ENSFCAP00000053707.1)
source                  1..314
                        mol_type = protein
                        organism = Sus scrofa
SEQUENCE: 19
RSCVIHLQCL PTGCLFSALH NGLPDGRLPL PDGRLPLPDG RLPLPDSRLP LPDGRLPLPD    60
GRLPLPDGRL PLPDGRLPLP DGRLPLPDGR LPLPDGRLPEG RLPLPDSHPP             120
LQDNLTQLSG EWNTLLVAAT NVDKISNGPF HGYICKVDVD VTNGTVVFNF SVMMNGRCTE   180
KSAVGTIGRD KFINIGSMNQ NLFNLFSVTS NTIAINVNTR RNTTKAFALL DTNGNIFNIG   240
YDSLGSLIIH TANVDTAGQT TQVFALLGKR LHPDDNDFAK FRELMRENNI PEENLIDMSK   300
TEKCPKKEKG TNPS                                                     314

SEQ ID NO: 20           moltype = AA   length = 175
FEATURE                 Location/Qualifiers
REGION                  1..175
                        note = Chimpanzee OBP (Ensembl ID ENSPTRP00000048681.3)
source                  1..175
                        mol_type = protein
                        organism = Pan troglodytes
SEQUENCE: 20
MALLLLSLGL SLITAQEFDP RNVMQRNYNM ARVSGVWYSI FMADDLNRIK ENGDLRVFVQ    60
NIEHLKNGSL KFDFEYMVQG ECVAVVVCE KTEKNGEYSI NYEGQNTVAV SETDYRLFIT   120
FHLQNFRNGT ETHTLALYET CKKYGLGSQN IINLTNKDPC YSKHYRSPPR PPMRE        175
```

```
SEQ ID NO: 21          moltype = AA  length = 210
FEATURE                Location/Qualifiers
REGION                 1..210
                       note = OBP::GQ20::KP (recombinant protein)
source                 1..210
                       mol_type = protein
                       organism = synthetic construct
SEQUENCE: 21
QEPQPEQDPF ELSGKWITSY IGSSDLEKIG ENAPFQVFMR SIEFDDKESK VYLNFFSKEN    60
GICEEFSLIG TKQEGNTYDV NYAGNNKFVV SYASETALII SNINVDEEGD KTIMTGLLGK   120
GTDIEDQDLE KFKEVTRENG IPEENIVNII ERDDCPAGQG QGQGQGQGQG QGQGQGQGQG   180
QGQGQGQGQG QGQGQGQGGV CGPSPPCITT                                    210

SEQ ID NO: 22          moltype = AA  length = 349
FEATURE                Location/Qualifiers
REGION                 1..349
                       note = OBP::GQ20::CBM (recombinant protein)
source                 1..349
                       mol_type = protein
                       organism = synthetic construct
SEQUENCE: 22
QEPQPEQDPF ELSGKWITSY IGSSDLEKIG ENAPFQVFMR SIEFDDKESK VYLNFFSKEN    60
GICEEFSLIG TKQEGNTYDV NYAGNNKFVV SYASETALII SNINVDEEGD KTIMTGLLGK   120
GTDIEDQDLE KFKEVTRENG IPEENIVNII ERDDCPAGQG QGQGQGQGQG QGQGQGQGQG   180
QGQGQGQGQG QGQGQGQASP IGEGTFDDGP EGWVAYGTDG PLDTSTGALC VAVPAGSAQY   240
GVGVVLNGVA IEEGTTYTLR YTATASTDVT VRALVGQNGA PYGTVLDTSP ALTSEPRQVT   300
ETFTASATYP ATPAADDPEG QIAFQLGGFS ADAWTLCLDD VALDSEVEL               349
```

ODORANT-BINDING PROTEIN COMPOSITIONS, METHODS AND USES THEREOF

CROSS REFERENCE

This application is a continuation of Ser. No. 18/003,127, filed Dec. 22, 2022, which is a § 371 U.S. National Stage Entry of International Application No. PCT/IB2021/056011, filed Jul. 5, 2021, which claims the benefit of Portuguese Application No. 116561, filed Jul. 3, 2020, and European Application No. 20206292.3, filed Nov. 6, 2020, each of which are hereby incorporated by reference in their entirety.

SEQUENCE LISTING

The instant application contains a Sequence Listing which has been submitted electronically in XML format and is hereby incorporated by reference in its entirety. Said XML copy, created on Dec. 13, 2023, is named 63230-716.301_Sequence_Listing.xml and is 32,435 bytes in size.

TECHNICAL FIELD

The present disclosure relates to a mechanism of adsorption and dissociation involving fragrance molecule and an odorant-binding protein (OBP-I) regulated simultaneously by human sweat and temperature. This system can be used in cosmetic formulations where the fragrances are released upon presence of sweat at body temperature.

BACKGROUND

Odorant-binding proteins (OBPs) are small water-soluble proteins, belonging to lipocalins superfamily.[1-2] They are responsible to transport hydrophobic odorous molecules, called odorants, in their calyx-shaped cavity, across the aqueous mucus barrier towards the olfactory receptors, where a cascade of transduction signal is traduced in the brain's interpretation.[3-4] These proteins are also described as involved in removing odorants from the olfactory receptors after their stimulation.[5-6]

Several mammalian odorant-binding proteins have been identified and some of them isolated from nasal mucus such as bovine, pig, boar, panda, mice, rats and humans.[7-13]

DNA sequences of mammalian OBPs present low similarity: porcine OBP (OBP-1) and human OBP (hOBP$_{IIa}$) present only 13.9% of DNA sequence similarity; OBP-1 and bovine OBP present 42.7%.[4] Despite wide genetic variability between OBPs from different mammalian species, lipocalin members present few characteristic signatures that allow their identification as the case of the conserved tertiary structure, presenting a 6-barrel structure composed by eight β-strands linked by seven loops and connected to a short α-helix close to the C-terminus and a ninth β-strand followed by the disordered C-terminal tail.[14-16] The structure of OBPs is highly stable and resistant to degradation by temperature, organic solvents, pH variation, or proteolytic digestion.[17-18] [19] The FT-IR spectra for porcine OBP revealed a structure exceptionally stable to thermal denaturation (up to 80° C.), particularly in the presence of a ligand.[20] Furthermore, vertebrate OBPs show capacity to reverse the unfolding of protein even after denaturation.[20]

Human body produces unpleasant odours associated with stress, anxiousness, nervousness and physical exercise.[21] To prevent or reduce their occurrence, antibacterial agents and fragrances are commonly added to cosmetic formulations. However, drawbacks related with the limited effect against different odours and with the residual amount of these deodorants are detected in clothing and skin.[22]

OBPs have affinity for several molecules associated with odorific feeling. All those molecules are volatile and detected by OBPs at very low concentrations, being a system highly sensitive. The fast responsive time of the OBPs and the high stability of these proteins create an excellent biological element as biosensor for detection of the dangerous substances and pathogens, pesticides and drugs present in food or water[18, 23] as well as the potential use as deodorizer and medical diagnostics.[24-25]

Odorific molecules can be associated with pleasant or unpleasant feelings. OBP have affinities for all molecules associated with odors.[3-4] Fragrances are compositions containing odorific molecules with pleasant feeling.

The use of 1-aminoanthracene (1-AMA) as odour model molecule provides a capacity to measure the binding capacity of odorant-binding protein, by fluorescence assay. The free 1-AMA and 1-AMA bound to pig OBP-I can be quantified measuring the fluorescence with excitation wavelength at 295 nm. The maximum wavelength of 1-AMA bound to OBP-I is shifted from 537 nm to 481 nm.[20] The non-fluorescence odorant can be measured by competitive assays or by gas chromatography-mass spectrometry.

The following works already reported the interaction between OBPs and odour model molecules, as well as with lipidic structures such as liposomes.

Filipa Gonçalves et al (2018) "Two Engineered OBPs with opposite temperature-dependent affinities towards 1-aminoanthracene" mentions two recombinant proteins based on pig OBP sequence (i) truncated OBP (tOBP-F44A/F66A) obtained from the deletion of the first 16 residues of the N-terminal and the replacement of two phenylalanine residues at the binding pocket by alanine residues (F44A and F66A), and (ii) OBP::GQ$_{20}$::SP-DS3 resulted of the fusion of OBP-I with a spacer of 20 repetitions of glycine-glutamine residues and the anchor peptide SP-DS3.[34] Experimental and molecular modelling data showed that 1-AMA model ligand binds preferentially to tOBP-F44A/F66A at 25° C. while ligand binds to OBP::GQ$_{20}$::SP-DS3 favourably at 37° C.[34]

Filipa Gonçalves et al (2018) "OBP fused with cell-penetrating peptides promotes liposomal transduction" report the fusion of porcine OBP with cell-penetrating peptides (CPPs, e.g. TAT, Pep-1 and pVEC). The study revealed different efficiencies on 1-AMA transduction into liposomes.[30]

Filipa Gongalves et al (2018) "1-Aminoanthracene Transduction into Liposomes Driven by Odorant-Binding Protein Proximity" discloses the design of two fusion proteins based on pig OBP fused with anchor peptide SP-DS3[32] in absence and presence of a spacer (GQ$_{20}$). This work demonstrated that the 1-AMA transduction into liposomes is driven by proximity of protein anchored to liposomal membrane (advantage for absence of spacer).[33]

Filipa Gonçalves et al (2019) "Release of Fragrances from Cotton Functionalized with Carbohydrate-Binding Module Proteins" discloses the design of fusion protein based on pig OBP fused with a spacer (GQ$_{20}$) and a carbohydrate binding module (CBM). The work demonstrated the affinity of protein to one fragrance (β-citronellol) and the release of this fragrance from cotton in presence of sweat.[25] Regardless, the release capacity in the presence of sweat is inferior as compared to the native OBP.

Alessandro Capo et al (2018) "The porcine odorant-binding protein as molecular probe for benzene detection"

discloses pig odorant-binding protein to be used as probe for benzene detection in atmosphere, through fluorescence assay.[28]

Nunzio Cennamo et a, (2015) "Easy to Use Plastic Optical Fiber-Based Biosensor for Detection of Butanal" reports the detection of butanal (20-1000 µM) by porcine odorant-binding protein through competitive assay. This aldehyde is very toxic, exhibiting high risks for human health like cytotoxicity and cancer. The authors describe an optical biosensor to detect butanol in liquid samples.[27]

Carla Silva et al (2014) "Odorant binding proteins: a biotechnological tool for odour control" discloses the application of porcine odorant-binding protein for release of fragrances from a cotton fabric to mask smoke odour. The authors confirmed the functionalization of OBP on fabrics. They tested only the release of one fragrance from textile. Contrary to the work of Silva et al., the present disclosure includes the release mechanism of different fragrances or other molecules as response of human perspiration with upper efficiency. Additionally, the subject-matter of the present disclosure is suitable for use in textile and cosmetic fields.

Paolo Pelosi et al (2014) "Structure and biotechnological applications of odorant-binding proteins" discloses the possibility of OBPs to be used as a sensor to detect volatile and slow release of odorant molecules.

Lei Han et al (2014) "Operating Mechanism and Molecular Dynamics of Pheromone-Binding Protein ASP1 as Influenced by pH" indicates pheromone-binding protein ASP1 as binds odorants at low pH and the dissociation respond to pH change. The authors describe the benefit of this research in biotechnology and agriculture. The results were determined by molecular docking and dynamics simulations.

Alberto Mazzini et al (2007) "Dissociation and unfolding of bovine odorant binding protein at acidic pH" discloses the structure of bovine OBP at neutral and acidic pH, by molecular simulation.

Mariella Parisi et al (2003) "Unfolding and refolding of porcine odorant binding protein in guanidinium hydrochloride: equilibrium studies at neutral pH" discloses the denaturant effect of guanidinium hydrochloride, a well-known chaotropic agent, in folding/unfolding of protein. The aim of this fundamental study was to understand the structure of the OBP protein, in particular its unfolding and refolding process.

Document WO 0123890A1 discloses a detector array based on sensing elements within a solid support with use for clinical samples or cell extracts, in gaseous state. It is an immunoassay utilizing viral peptides.

Document EP0335654A3 discloses the method for gene isolation of odorant-binding protein from rat and a protein production method.

Document WO2001012806A3 described OBPII as a fixer of hydrophobic ligands such as odours that can be used for personal hygiene, agri-food system and nutritional and therapeutic uses.

These facts are disclosed in order to illustrate the technical problem addressed by the present disclosure.

GENERAL DESCRIPTION

The present disclosure is related to adsorption and dissociation mechanism of native odorant-binding protein (OBP-I), in particular pig OBP-I (SEQ. ID NO. 1), and OBP fused with linker GQ 20× and KP peptide (OBP::$GQ_{20}$::KP, SEQ. ID NO. 21). These proteins have a negative charge of approximately −20 (pH 7.4) due to the high content in aspartic acid and glutamic acid residues. The isoelectric point value of these proteins are between 4.08 and 4.65.[26]

In an embodiment, the solution here disclosed can have a high impact in human social life that are associated with perspiration issues. The system has several advantages including the use of bioinspired cosmetic bioingredients (green solutions) without damaging for the ecosystems.

The mechanism here disclosed divulge that odorant-binding protein, in particular porcine odorant-binding protein (OBP-1), presents high affinity (adsorption) to fragrances in 50 mM Tris-HCl pH 7.5 buffer, at 37° C. The affinity constant (Ka) of OBP-I was of 4.00±0.03 µM. On the other hand, OBP-I presents a reverse mechanism, i.e., the dissociation of fragrance from its binding pocket with reduced Ka (0.20 t0.02 µM) when in exposition of perspiration (sweat), even at different pH (range of 4.0-8.5, Table 2). Similarity, OBP::$GQ_{20}$::KP presents high affinity to fragrances in buffer, at 37° C. (Ka=4.00±0.04 µM) that is reduced in presence of an electrolyte solution, such as sweat (Ka=0.59±0.01 µM). Therefore, OBPs presents reduced affinity when in contact with perspiration, releasing the fragrance in this condition.

Surprisingly, OBP::$GQ_{20}$::KP (SEQ ID NO. 21) showed 6.8× more fragrance release in presence of sweat versus the presence of buffer. These values are superior to the values reported in state of art, in particular to the values reported for OBP::$GQ_{20}$::CBM (SEQ ID NO. 22), where the release mechanism showed 1.3× release of fragrance in presence of sweat.[25]

The adsorption and dissociation mechanism of porcine odorant-binding protein can be done in a repeated manner.

Human sweat can be used as a trigger to release/dissociate a fragrance from OBP-I. Therefore, the subject-matter of the present disclosure can be used in skin care products as well as in textile items, in particular clothes.

In an embodiment, the present disclosure relates to a protein with an amino acid sequence similar to mammalians odorant-binding proteins to be incorporated in formulations for cosmetic or textile applications.

In an embodiment, the native form of odorant-binding protein may be from pig, human, dog, cat, rat, mouse, cow, boar, panda, Chinese hamster, Meishan pig, Guinea pig, Tibetan pig, horse, dolphin and chimpanzee.

In an aspect of the present disclosure, applications of the present subject-matter may be based on the release of odorant molecules from odorant-binding protein, triggered by electrolyte solutions at body temperature.

In an embodiment, the electrolyte solution refers to a solution with a NaCl concentration higher than 9.5 grams/L, in particular to a solution with a NaCl concentration ranging from 9.5 to 45 grams/L. Preferably, the electrolyte solution is human sweat, pet sweat, salty water or micellar water.

In an embodiment, human sweat may comprise water, lactic acid, urea and minerals, such as sodium, potassium, calcium, and magnesium.

In an embodiment, cosmetic applications may be for skin and hair care. Skin care applications may be related with OBPs formulated in specialty formulations for skin creams, lipsticks, lips creams and face mask powders, face and body creams, skin clarifiers, primers and foundations.

In a further embodiment, hair care applications may be related with OBPs formulated in eyelash mascaras, hair shampoos, hair serum, hairs masks, hair conditioners, or hair coloration creams.

The present disclosure relates to a release composition comprising an isolated or artificial protein with at least 90% of identity with an amino acid sequence selected from the following list: SEQ. ID NO. 1, SEQ. ID NO. 2, SEQ. ID NO. 3, SEQ. ID NO. 4, SEQ. ID NO. 5, SEQ. ID NO. 6, SEQ. ID NO. 7, SEQ. ID NO. 8, SEQ. ID NO. 9, SEQ. ID NO. 10, SEQ. ID NO. 11, SEQ. ID NO. 12, SEQ. ID NO. 13, SEQ. ID NO. 14, SEQ. ID NO. 15. SEQ. ID NO. 16, SEQ. ID NO. 17, SEQ. ID NO. 18, SEQ. ID NO. 19, SEQ. ID NO. 20, SEQ. ID NO. 21, or mixtures thereof, preferably 91% identical, 92% identical, 93% identical, 94% identical, 95% identical, 96% identical, 97% identical, 98% identical, 99% identical or identical; an active agent selected from a list comprising a deodorizing agent, a natural essence, a fragrance, a moisturizing agent, or mixtures thereof; wherein the active agent is bounded to the protein; and wherein the protein releases the active agent in the presence of an electrolyte solution, at a temperature between 10-60° C.

In an embodiment, the release composition comprises an isolated or artificial unmodified protein with at least 90% of identity with an amino acid sequence selected from the following list: SEQ. ID NO. 1, SEQ. ID NO. 2, SEQ. ID NO. 3, SEQ. ID NO. 4, SEQ. ID NO. 5, SEQ. ID NO. 6, SEQ. ID NO. 7, SEQ. ID NO. 8, SEQ. ID NO. 9, SEQ. ID NO. 10, SEQ. ID NO. 11, SEQ. ID NO. 12, SEQ. ID NO. 13, SEQ. ID NO. 14, SEQ. ID NO. 15. SEQ. ID NO. 16, SEQ. ID NO. 17, SEQ. ID NO. 18, SEQ. ID NO. 19, SEQ. ID NO. 20, SEQ. ID NO. 21, or mixtures thereof, preferably 91% identical, 92% identical, 93% identical, 94% identical, 95% identical, 96% identical, 97% identical, 98% identical, 99% identical or identical.

Methods for the alignment of sequences for comparison are well known in the art, such methods include GAP, BESTFIT, BLAST, FASTA and TFASTA. GAP uses the algorithm of Needleman and Wunsch ((1970) J Mol Biol 48: 443-453) to find the global (over the whole the sequence) alignment of two sequences that maximizes the number of matches and minimizes the number of gaps. The BLAST algorithm (Altschul et al. (1990) J Mol Biol 215: 403-10) calculates percent sequence identity and performs a statistical analysis of the similarity between the two sequences. The software for performing BLAST analysis is publicly available through the National Centre for Biotechnology Information (NCBI). Global percentages of similarity and identity may also be determined using one of the methods available in the MatGAT software package (Campanella et al., BMC Bioinformatics. 2003 Jul. 10; 4:29. MatGAT: an application that generates similarity/identity matrices using protein or DNA sequences). Minor manual editing may be performed to optimise alignment between conserved motifs, as would be apparent to a person skilled in the art. The sequence identity values, which are indicated in the present subject matter as a percentage were determined over the entire amino acid sequence, using BLAST with the default parameters.

In an embodiment, the composition of the present subject-matter comprises 0.01 to 5000 µM of the unmodified protein.

In an embodiment, the composition of the present subject-matter comprises 0.01 to 5000 µM of the protein.

In another embodiment, the release composition comprises 0.1 µM to 2 M of active agent, preferably 0.2 µM to 1 M.

In an embodiment, the protein has an affinity constant of 1-4.5 µM to the active agent, in water or buffer solutions, preferably Tris-HCl, phosphate solution, and/or phosphate buffered saline. In a further embodiment, the affinity constant of the protein to the active agent ranges between 0.1-0.99 µM in the electrolyte solution, preferably in sweat.

The present disclosure relates to a fragrance release composition comprising: 0.01 to 5000 µM of an isolated or artificial protein with at least 90% of identity with an amino acid sequence selected from the following list: SEQ. ID NO. 1, SEQ. ID NO. 2, SEQ. ID NO. 3, SEQ. ID NO. 4, SEQ. ID NO. 5, SEQ. ID NO. 6, SEQ. ID NO. 7, SEQ. ID NO. 8, SEQ. ID NO. 9, SEQ. ID NO. 10, SEQ. ID NO. 11, SEQ. ID NO. 12, SEQ. ID NO. 13, SEQ. ID NO. 14, SEQ. ID NO. 15. SEQ. ID NO. 16, SEQ. ID NO. 17, SEQ. ID NO. 18, SEQ. ID NO. 19, SEQ. ID NO. 20, SEQ. ID NO. 21 or mixtures thereof; 0.1 µM to 2 M of an active agent selected from a list comprising a deodorizing agent, a natural essence, a fragrance, a moisturizing agent, or mixtures thereof; wherein the active agent is bounded and/or entrapped to the protein; and wherein the protein releases the active agent in the presence of an electrolyte solution, at a temperature between 10-70° C., preferably 10-60° C.; wherein the affinity constant of the protein to the active agent, in water, ranges between 1-4.5 µM; wherein the active agent has a molecular weight from 20 to 1000 g/mol; wherein the electrolyte solution is sweat, salty water or micellar water.

In an embodiment, the active agent has a molecular weight between 20 to 1000 g/mol, preferably 75-300 g/mol. In a further embodiment, the active agent is a fragrance molecule. In a yet further embodiment, the bioactive agent comprises a functional group selected from aromatic, aldehyde or alcohols. In a yet further embodiment, the active agent is a fragrance molecule, selected from a list comprising the molecules listed in Table 1.

TABLE 1

List of fragrances and their properties.

| CAS# | Name | Odor description | Chemical Family | MW (g/mol) |
| --- | --- | --- | --- | --- |
| 85213-22-5 | 2-acetyl-1-pyrroline | roasted/bread | ketone | 111.14 |
| 8000-41-7 | α-terpineol | lilac | alcohol/terpene | 154.25 |
| 502-99-8 | β-ocimene | sweet herbal | hydrocarbon/terpene | 136.24 |
| 140-11-4 | benzyl acetate | strawberry/pear | ester | 150.17 |
| 123-86-4 | butyl acetate | banana | ester | 116.16 |
| 76-22-2 | camphor | camphora | ketone/terpene | 152.24 |
| 6485-40-1 | carvone | mint | ketone/terpene | 150.22 |
| 5392-40-5 | citral | lemon/citrus | aldehyde/terpene | 152.24 |
| 106-22-9 | citronellol | citronella/rose-like | alcohol/terpene | 156.27 |
| 91-64-5 | coumarin | sweet vanilla/pleasant | lactone/aromatic | 146.15 |
| 431-03-8 | diacetyl | buttery | ketone | 86.09 |
| 97-53-0 | eugenol | cloves | aromatic alcohol | 164.20 |

TABLE 1-continued

List of fragrances and their properties.

| CAS# | Name | Odor description | Chemical Family | MW (g/mol) |
|---|---|---|---|---|
| 6413-10-1 | fructone | apple | ester | 174.19 |
| 706-14-9 | gamma decalactone | coconut | lactone | 170.25 |
| 104-61-0 | gamma nonalactone | peach/fruity | lactone | 156.23 |
| 106-24-1 | geraniol | floral/sweet rose | terpene | 154.24 |
| 24851-98-7 | hedione | floral/jasmine | ester | 226.32 |
| 123-92-2 | isoamyl acetate | pear/banana | ester | 130.19 |
| 67920-63-2 | lilac aldehyde | floral/lilac | aldehyde/terpene | 168.24 |
| 5989-27-5 | limonene | citric | terpene | 136.23 |
| 126-91-0 | linalool | lavender/bergamot | terpene | 154.25 |
| 55066-48-3 | mefrosol | floral/rose | alcohol | 178.27 |
| 2216-51-5 | menthol | peppermint | alcohol | 156.26 |
| 623-42-7 | methyl butyrate | apple/pineapple | ester | 102.13 |
| 123-35-3 | myrcene | herbal/woody | terpene | 136.24 |
| 80-56-8 | pinene | pine | terpene | 136.24 |
| 357650-26-1 | pomarose | plums/apples rose | ketone | 166.26 |
| 89-82-7 | pulegone | peppermint | ketone/terpene | 152.24 |
| 65113-99-7 |sandalore | sandalwood | alcohol | 210.36 |
| 121-33-5 | vanilin | vanilla | aldehyde/aromatic | 152.15 |

In an embodiment, the release of the active agent occurs during 30 seconds to 24 h.

In an embodiment, electrolyte solution has a pH between 4.0-8.5. In a further embodiment, the electrolyte solution is sweat, salty water or micellar water, preferably human sweat or pet sweat.

In an embodiment, the unmodified protein is stable in polar and non-polar solvents, including methanol, butanol, benzene, ethanol and undecanol as well as buffer solutions, preferably Tris-HCl, phosphate, or phosphate buffered saline (PBS)). In a further embodiment, the unmodified protein is also stable in temperatures between 18-70° C., preferably 18-60° C., and in a pH range of 4.0-10.0.

In an embodiment, the protein is stable in polar and non-polar solvents, including methanol, butanol, benzene and undecanol as well as buffer solutions (Tris-HCl, phosphate, PBS). In a further embodiment, the protein is also stable in temperatures between 18-70° C., preferably 18-60° C., and in a pH range of 4.0-10.0.

In an embodiment, the release of the active agent from the protein occurs at 20-40° C.

In an embodiment, the composition further comprises glycerol, erythritol, arabitol, sorbitol, mannitol, xylitol, mannisdomannitol, glucosylglycerol, glucose, fructose, sucrose, trehalose, isofluoroside, dextrans, levans, polyethylene glycol, salts of chloride, citrate, sulfates, acetate or phosphates, or mixtures thereof.

An aspect of the present disclosure comprises a kit or article comprising the composition described in the present subject-matter. In an embodiment, the article comprising said composition can be selected from a list comprising fabric, textiles, fibers, clothes, scarfs, hats, gloves, socks and turbans, shoes, insoles, bags, handbags, detergents, creams, lotions, foams, perfumes, softeners, aerosols, deodorants, lipsticks, lip creams, face mask powders, face and body creams, skin clarifiers, primers, foundations, hair shampoos, hair serum, hairs masks, hair conditioners or hair coloration creams.

The present disclosure also relates to the use of the fragrance release composition described in the present subject-matter in cosmetics, preferably as a cosmetic agent/composition, more preferably skin care or hair care; as well as the use of said composition in the textile industry.

The present disclosure also relates to the use of the fragrance release composition as a deodorant agent/composition.

BRIEF DESCRIPTION OF THE DRAWINGS

The following FIGURES provide preferred embodiments for illustrating the disclosure and should not be seen as limiting the scope of invention.

FIG. 1: Schematic representation Sodium dodecyl sulfate and polyacrylamide (SDS-PAGE) gel electrophoresis under reducing conditions (A), and circular dichroism (CD) spectrum (B) of native pig odorant-binding protein. Mw: Precision Plus Protein™ standards (BioRad).

DETAILED DESCRIPTION

The present disclosure concerns the method of manufacture of a fragrance/protein complex and the adsorption and dissociation mechanism of native odorant-binding protein (OBP-I), in particular pig OBP-I, and native protein fused with $GQ_{20}$ and KP peptide. This mechanism involves the release of active agents, preferably odorific molecules (or fragrances), in response to human perspiration.

The present disclosure presents high impact in textile and cosmetic fields, particularly in the release of fragrances from lotion and cream base products as well as textile fabrics, awarding a green solution.

In an embodiment, the produced odorant-binding protein and fragrance/protein complex are very soluble and stable at different solvents (like methanol, butanol, benzene and undecanol) and different range of temperature (18-60° C.) and different range of pH (4.0-10.0).[12, 27-29]

In a further embodiment, the mixture of odorific molecules and the OBP-I or OBP::$GQ_{20}$::KP proteins showed improved results regarding the affinity constants in a buffer solution and in sweat (Table 2). In particular, the lower Ka in sweat enforces the use of OBP proteins when sweat-triggered responses are envisaged. Notably, the adsorption and dissociation mechanism by the proteins is reversible. In response to human perspiration at different range of pH (pH 4.0-8.5) the disclosed proteins released more than 20× to 6.8× (OBP-I and OBP::$GQ_{20}$::KP, respectively) of odorific molecules compared with other fusion proteins based on porcine odorant-binding protein (Table 2). Thus, the release of fragrance occurs in response of perspiration and it is independent of pH of sweat of each human. Additionally, the fragrance release occurs at least during 0.5-24 h.

In an embodiment, a variety of active agents, including deodorizing agents, natural essences, fragrance agents, moisturizing agents, or mixtures thereof, can be used in the complex formation, allowing a wide range of cosmetic uses. In particular, pleasant odorific molecules (of different size and shape) showed great affinity to the odorant-binding protein, in particular porcine odorant-binding protein.

In an embodiment, the odorific molecules used in the present disclosure belong to different functional groups (aromatic, aldehyde, alcohols). In a further embodiment the odorific molecules comprise molecules with a molecular weight ranging from 20.00 to 1000.00 g/mol, and the concentration varies from 0.2-2000 µM.

In an embodiment, odorific molecules have a molecular weight between 75 to 300 g/mol.

In an embodiment, the system efficiently responded to human perspiration, releasing fragrances over time. Importantly, the system did not respond against the water existent in human body, giving specificity and robustness to the subject-matter presented in this disclosure. Without this selectivity, i.e., if the system responded to water, the OBP protein would immediately release the odorific molecules when in contact with the skin.

EXAMPLE

In an embodiment, native porcine odorant-binding protein (OBP-1) and OBP-I fused with a spacer glycine-glutamine, repeated 20× ($GQ_{20}$) and with a carbohydrate-binding module (OBP::$GQ_{20}$::CBM) were cloned in plasmid pET28a and transformed into Escherichia coli BL21(DE3). The proteins were expressed and purified through Nickel magnetic beads with specificity to His-tag present in the protein's N-terminal. 10 µM of protein were loaded on sodium dodecyl sulfate and polyacrylamide (SDS-PAGE) gel electrophoresis under reducing conditions. The same concentration was used to determine the structure of proteins by circular dichroism (CD) spectroscopy.

The protein purified in laboratory reveals a high level of purity (observed by SDS-PAGE gel, FIG. 1-A) and secondary structure in barrel, a consequence of the presence of a high number of β-sheets, as analysed by circular dichroism spectroscopy (FIG. 1-B).

In an embodiment, the pure odorant-binding protein was lyophilized and used in further procedures. To determine the affinity of the odorant-binding protein to odour molecules, 1-aminoanthracene (1-AMA) was used as an odour model molecule. Increased concentrations of fluorescent ligand model 1-aminoanthracene (1-AMA) were added to 1 µM of protein, and the formation of ligand/protein complex was quantified after 1 h at 37° C. by fluorescence emission at 481 nm (excitation at 295 nm).[30] Dissociation constant (Kd) was determined from a plot of fluorescence intensity versus concentration of ligand, obtained with a standard non-linear regression method, described in Malpeli et al. (1998).[31] The affinity behaviour of protein in presence of sweat solution was performed through a competitive fluorescence assay. Here, 1 µM of protein was mixed with 2 µM of 1-AMA and incubated at 37° C. for 1 h. After this period, increased volumes of sweat solution were added to the complex and incubated at same conditions.

In an embodiment, the sweat solution was prepared as indicated in AATCC method 15-2009 "Colorfastness to Perspiration". The pH of the prepared solution varied between 4.0 and 8.5. In accordance with its composition, the sweat solution is also regarded as electrolyte solution.

In a further embodiment, fluorescence emission at 481 nm (excitation at 295 nm) was recorded and the dissociation constant (Kd) calculated. The association constant (Ka) was calculated by formula Kd=1/Ka.

In an embodiment, the release of fragrance was quantified by gas chromatography-mass spectrometry (GC-MS). Increased concentrations of fragrance were used in different vials and the fragrance in headspace quantified performing the calibration curve (area of peak vs fragrance concentration). The fragrance was incubated with the odorant-binding protein at 37° C. Sweat solution was added and the fragrance release determined after several periods of time (0.5-24 h) of perspiration exposition.

In an embodiment, as comparative data, porcine odorant-binding protein was fused with a spacer $GQ_{20}$ and a carbohydrate-binding module (CBM), as previously reported.[25] Through the fusion of $CBM_{N1}$ (PDB ID 1ULP) of endoglucanase C from Cellulomonas fimi, the OBP has a specific affinity to cotton. The modified protein showed a high association constant (Ka=4.17±0.05 µM) that decreased for Ka=3.16±0.02 µM when a sweat solution was added. Native OBP-I (SEQ ID No. 1) and OBP::$GQ_{20}$::KP (SEQ ID NO. 21) showed an association constant very similar (Ka=4.00±0.03 µM) to the value obtained for OBP::$GQ_{20}$::CBM (SEQ ID NO. 22, Ka=4.17±0.05). However, the addition of the sweat solution had a remarkable effect in the constant of affinity of the native protein (Ka=0.20±0.02 µM) and of the OBP::$GQ_{20}$::KP (Ka=0.59±0.01 µM). A high reduction of affinity was observed, 20× using native OBP (SEQ ID NO. 1) and 6.8× using OBP::$GQ_{20}$::KP (SEQ ID NO. 21), as compared with the value quantified for protein fused with CBM (SEQ ID NO 22), where a reduction of only 1.3× was verified (Ka=3.16±0.02 Table 2). Thus, the release of fragrance by OBP-I and OBP fused with KP is evident in response of perspiration.

TABLE 2

Affinity constant (Ka) of native OBP-I (SEQ ID NO. 1) and fusion proteins based on OBP, SEQ ID NO. 21 and SEQ ID NO 22. SEQ ID NO 22 was used as comparative data. Values are the mean of 2 independent experiments at 37° C.

| Protein | Ka in buffer (µM) | Ka in sweat (µM) |
|---|---|---|
| Native porcine OBP (OBP-I)-SEQ ID NO 1 | 4.00 ± 0.03 | 0.20 ± 0.02 |
| OBP::$GQ_{20}$::KP-SEQ ID NO 21 | 4.00 ± 0.04 | 0.59 ± 0.01 |
| OBP::$GQ_{20}$::CBM (fusion protein)[25]-SEQ ID NO 22 | 4.17 ± 0.05 | 3.16 ± 0.02 |

In an embodiment, the following protein sequences can be incorporated in different substrates in order to release fragrances in the presence of sweat. In this regard, substrates can be selected from a list comprising textiles, fabrics, skin care products, hair care products, among others.

LIST OF PROTEIN SEQUENCES

The sequences of protein are described by one letter code of amino acids. The code is as follows:

| One letter code | Amino acid |
|---|---|
| A | Alanine |
| C | Cysteine |
| D | Aspartic acid |
| E | Glutamic acid |
| F | Phenylalanine |
| G | Glycine |
| H | Histidine |
| I | Isoleucine |
| K | Lysine |
| L | Leucine |
| M | Methionine |
| N | Asparagine |
| P | Proline |
| Q | Glutamine |
| R | Arginine |
| S | Serine |
| T | Threonine |
| V | Valine |
| W | Tryptophan |
| Y | Tyrosine |

```
Pig OBP (PDB ID 1DZK)
                                                     SEQ ID NO. 1
QEPQPEQDPFELSGKWITSYIGSSDLEKIGENAPFQVFMRSIEFDDKESKVYLNFFSKENGICEE

FSLIGTKQEGNTYDVNYAGNNKFVVSYASETALIISNINVDEEGDKTIMTGLLGKGTDIEDQDLE

KFKEVTRENGIPEENIVNIIERDDCPA

Human OBP_IIa (UniProt ID Q9NY56)
                                                     SEQ ID NO. 2
MKTLFLGVTLGLAAALSFTLEEEDITGTWYVKAMVVDKDFPEDRRPRKVSPVKVTALGGGNLEAT

FTFMREDRCIQKKILMRKTEEPGKFSAYGGRKLIYLQELPGTDDYVFYCKDQRRGGLRYMGKLVG

RNPNTNLEALEEFKKLVQHKGLSEEDIFMPLQTGSCVLEH

Human OBP1lb (UniProt ID Q9NPH6)
                                                     SEQ ID NO. 3
MKTLFLGVTLGLAAALSFTLEEEDITGTWYVKAMVVDKDFPEDRRPRKVSPVKVTALGGGKLEAT

FTFMREDRCIQKKILMRKTEEPGKYSAYGGRKLMYLQELPRRDHYIFYCKDQHHGGLLHMGKLVG

RNSDTNREALEEFKKLVQRKGLSEEDIFTPLQTGSCVPEH

Mouse OBP (UniProt ID OBP1A)
                                                     SEQ ID NO. 4
MAKFLLLALTFGLAHAAMEGPWKTVAIAADRVDKIERGGELRIYCRSLTCEKECKEMKVTFYVNE

NGQCSLTTITGYLQEDGKTYKTQFQGNNRYKLVDESPENLTFYSENVDRADRKTKLLFILGHGPL

TSEQKEKFAELAEEKGIPAGNIREVLITDYCPE

Mouse OBP2A (UniProt ID Q8K1H9)
                                                     SEQ ID NO. 5
MKSLLLTILLLGLVAVLKAQEAPPDDLVDYSGIWYAKAMVHNGTLPSHKIPSIVFPVRIIALEEG

DLETTVVFWNNGHCREFKFVMKKTEEPGKYTAFHNTKVIHVEKTSVNEHYIFYCEGRHNGTSSFG

MGKLMGRDSGENPEAMEEFKNFIKRMNLRLENMFVPEIGDKCVESD

Mouse OBP1B (UniProt ID A2AEP0)
                                                     SEQ ID NO. 6
MMVKFLLLALVFGLAHVHAHDHPELQGQWKTTAIMADNIDKIETSGPLELFVREITCDEGCQKMK

VTFYVKQNGQCSLTTVTGYKQEDGKTFKNQYEGENNYKLLKATSENLVFYDENVDRASRKTKLLY

ILGKGEALTHEQKERLTELATQKGIPAGNLRELAHEDTCPE

Rat OBP (PDB ID 3FIQ)
                                                     SEQ ID NO. 7
HHENLDISPSEVNGDWRTLYIVADNVEKVAEGGSLRAYFQHMECGDECQELKIIFNVKLDSECQT

HTVVGQKHEDGRYTTDYSGRNYFHVLKKTDDIIFFHNVNVDESGKETNVILVAGKREDLNKAQKQ

ELRKLAEEYNIPNENTQHLVPTDTCNQ
```

-continued

Rat OBP (PDB ID 3ZQ3)
SEQ ID NO. 8
MRGSHHHHHHTDPEEASFERGNLDVDKLNGDWFSIVVASDKREKIEENGSMRVFVQHIDVLENSL
GFTFRIKENGVCTEFSLVADKTAKDGEYFVEYDGENTFTILKTDYDNYVMFHLVNVNNGETFQLM
ELYGRTKDLSSDIKEKFAKLCVAHGITRDNIIDLTKTDRCLQA

Rat OBP (UniProt ID P08937)
SEQ ID NO. 9
MVKFLLIVLALGVSCAHHENLDISPSEVNGDWRTLYIVADNVEKVAEGGSLRAYFQHMECGDECQ
ELKIIFNVKLDSECQTHTVVGQKHEDGRYTTDYSGRNYFHVLKKTDDIIFFHNVNVDESGRRQCD
LVAGKREDLNKAQKQELRKLAEEYNIPNENTQHLVPTDTCNQ Bovine OBP (PDB ID 1OBP)
SEQ ID NO. 10
AQEEEAEQNLSELSGPWRTVYIGSTNPEKIQENGPFRTYFRELVFDDEKGTVDFYFSVKRDGKWK
NVHVKATKQDDGTYVADYEGQNVFKIVSLSRTHLVAHNINVDKHGQTTELTGLFVKLNVEDEDLE
KFWKLTEDKGIDKKNVVNFLENEDHPHPE Boar OBP (PDB ID 1GM6)
SEQ ID NO. 11
HKEAGQDVVTSNFDASKIAGEWYSILLASDAKENIEENGSMRVFVEHIRVLDNSSLAFKFQRKVN
GECTDFYAVCDKVGDGVYTVAYYGENKFRLLEVNYSDYVILHLVDVNGDKTFQLMEFYGRKPDVE
PKLKDKFVEICQQYGIIKENIIDLTKIDRCFQLRGSGGVQESSAE Panda OBP (PDB ID 5NGH)
SEQ ID NO. 12
HEEGNDVRRNFDVSKISGYWYSVLLASDVREKTEENSSMRVFVNHIEVLSNSSLLFNMHIKVDGK
CTEIALVSDKTEKDGEYSVEYDGYNVFRIVETDTYDYIIFHLVNFKEKDSFQMMELSAREPDTSE
EVRKRFVEYCQKHGIVKENIFDLTEVDRCLQARGSEKA Chinese hamster OBP (Ensembl ID ENSCGRP00015014591.1)
SEQ ID NO. 13
MVKFLLLAFALSVSCAHHKIPEISPSEVDGKWRTLYIGADNTEKVIQGGPLRAYFRHMECSDECQ
TLTITFNTKEEGKCQTHTVVGRKDEDGQYKTGFSGNNDFHVVEKADGIIIFHNVNVDSSGKKTNV
ILVAGKGKSLSKEQKERLENIAKEFDISKENIQHLVPTDTCDQ Meishan pig OBP (Ensembl ID ENSSSCP00040041163.1)
SEQ ID NO. 14
MKSLLLSLVLGLVCAQEPQPEQDPFVLSGKWITSYIGSSDLEKIGENAPFQVFMRSIEFDDKESK
VYLNFFSKENGICEEFSLIGTKQEGNTYDVNYAGNNKFVVSYASETALIISNINVDEEGDKTIMT
GLLGKGTDIEDQDLEKFKEVTRENGIPEENIVNIIERDDCPAK Horse OBP (Ensembl ID ENSECAP00000000103.2)
SEQ ID NO. 15
MQILLLSLVLGVVCAVQEPQSETDYSLFSGEWNTIYIGSSNIEKISENGPFRILLRRLDLDSAGD
RIIYTFFLKVNGQCTKISSLAIKTEENTYVCHYAGKNKFEILHLSKTAIIIDIVNEDEGGLVTKM
VALVGMLGDIQKEDIEKFKEVAKEKEIPEENIVNIINIDDCPTSE Guinea pig OBP ((Ensembl ID ENSCPOP00000016393.2)
SEQ ID NO. 16
MQILLLALTIGLAYAHQTLDPSEINGQWHTISIAADNVEKIGEGGPLRGYFHNLHCYDGCKNIGL
TFYVKLDGNCQRFDVLGAKQEDSDVYVAQYSGTNHFEVIGKKEDAIAFYNHNTDETGKETKMIVV
VARRDSLTEEEQQKLQEVAGEKGIPKDNIRYFRERDTCAQ Dog OBP ((Ensembl ID ENSCAFP00040020992.1)
SEQ ID NO. 17
MKILLLCLILVLACDAHLPLPNVLTQVSGPWKTLYVSSNNLDKIAENGPFRIYIRRINVDIPRLK
ILFSFFVKVDGECVEKSVEASIGQDNLINAHYAGGNYHQILDVTPNALIGYIVNVDDKGRITKLA
SLVGRGAHVNEEDIAKFKKLSREKGIPEENIIYLGDTDNCPNHE -continued Tibetan pig OBP (Ensembl ID ENSSSCP00015013912.1)
SEQ ID NO. 18
MKSLLLSLVLGLVCAQEPQPEQDPFELSGKWITSYIGSSDLEKIGENAPFQVFMRSIEFDDKESK

VYLNFFSKENGICEEFSLTGTKQEGNTYDVNYAGNNKFVVSYASETALIIANINVDEEGDKTIMT

GLLGKGTDIEDQDLEKFKEVTRENGIPEENIVNIIERDDCPAK

Cat felis OBP (Ensembl ID ENSFCAP00000053707.1)
SEQ ID NO. 19
RSCVIHLQCLPTGCLFSALHNGLPDGRLPLPDGRLPLPDGRLPLPDSRLPLPDGRLPLPDGRLPL

PDGRLPLPDGRLPLPDGRLPLPDGRLPLPDGRLPLPDGRLPLPEGRLPLPDSHPPLQDNLTQLSG

EWNTLLVAATNVDKISNGPFHGYICKVDVDVTNGTVVFNFSVMMNGRCTEKSAVGTIGRDKFINI

GSMNQNLFNLFSVTSNTIAINVNTRRNTTKAFALLDTNGNIFNIGYDSLGSLIIHTANVDTAGQT

TQVFALLGKRLHPDDNDFAKFRELMRENNIPEENLIDMSKTEKCPKKEKGTNPS

Chimpanzee OBP (Ensembl ID ENSPTRP00000048681.3)
SEQ ID NO. 20
MALLLLSLGLSLITAQEFDPRNVMQRNYNMARVSGVWYSIFMADDLNRIKENGDLRVFVQNIEHL

KNGSLKFDFEYMVQGECVAVVVVCEKTEKNGEYSINYEGQNTVAVSETDYRLFITFHLQNFRNGT

ETHTLALYETCKKYGLGSQNIINLTNKDPCYSKHYRSPPRPPMRE

OBP::GQ$_{20}$::KP (recombinant protein)
SEQ ID NO. 21
QEPQPEQDPFELSGKWITSYIGSSDLEKIGENAPFQVFMRSIEFDDKESKVYLNFFSKENGICEE

FSLIGTKQEGNTYDVNYAGNNKFVVSYASETALIISNINVDEEGDKTIMTGLLGKGTDIEDQDLE

KFKEVTRENGIPEENIVNIIERDDCPAGQGQGQGQGQGQGQGQGQGQGQGQGQGQGQGQGQGQ

GQGGVCGPSPPCITT

OBP::GQ$_{20}$::CBM (recombinant protein)
SEQ ID NO. 22
QEPQPEQDPFELSGKWITSYIGSSDLEKIGENAPFQVFMRSIEFDDKESKVYLNFFSKENGICEE

FSLIGTKQEGNTYDVNYAGNNKFVVSYASETALIISNINVDEEGDKTIMTGLLGKGTDIEDQDLE

KFKEVTRENGIPEENIVNIIERDDCPAGQGQGQGQGQGQGQGQGQGQGQGQGQGQGQGQGQGQ

GQASPIGEGTFDDGPEGWVAYGTDGPLDTSTGALCVAVPAGSAQYGVGVVLNGVAIEEGTTYTLR

YTATASTDVTVRALVGQNGAPYGTVLDTSPALTSEPRQVTETFTASATYPATPAADDPEGQIAFQ

LGGFSADAWTLCLDDVALDSEVEL

REFERENCES (1) Flower, D. R. The lipocalin protein family: structure and function. Biochem. J. 1996, 318, 1-14.
(2) Flower, D. R. Beyond the superfamily: the lipocalin receptors. Biochimica et biophysica acta 2000, 1482, 327-336.
(3) Breer, H. Olfactory receptors: molecular basis for recognition and discrimination of odors. Analytical and bioanalytical chemistry 2003, 377 (3), 427-33, DOI: 10.1007/s00216-003-2113-9.
(4) Tegoni, M.; Pelosi, P.; Vincent, F.; Spinelli, S.; Campanacci, V.; Grolli, S.; Ramoni, R.; Cambillau, C. Mammalian odorant binding proteins. Biochimica et biophysica acta 2000, 1482, 229-240.
(5) Bignetti, E.; Cattaneo, P.; Cavaggioni, A.; Damiani, G. The pyrazine-binding protein and olfaction. Comp. Biochem. Physiol. 1988, 90B, 1-5.
(6) Pevsner, J.; Hou, V.; Snowman, A. M.; Snyder, S. H. Odorant-binding protein: characterization of ligand binding. The Journal of biological chemistry 1990, 265 (11), 6118-6125.
(7) Bignetti, E.; Cavaggioni, A.; Pelosi, P.; Persaud, K. C.; Sorbi, R. T.; Tirindelli, R. Purification and characterisation of an odorant-binding protein from cow nasal tissue. Eur. J. Biochem. 1985, 149, 227-231.
(8) Dal Monte, M.; Andreini, I.; Revoltella, R.; Pelosi, P. Purification and characterization of two odorant-binding proteins from nasal tissue of rabbit and pig. Comp Biochem Physiol 1991, 99B (2), 445-451.
(9) Garibotti, M.; Navarrini, A.; Pisanelli, A. M.; Pelosi, P. Three Odorant-binding Proteins from Rabbit Nasal Mucosa. Chemical senses 1997, 22 (4), 383-390.
(10) Lazar, J.; Greenwood, D. R.; Rasmussen, L. E. L; Prestwich, G. D. Molecular and Functional Characterization of an Odorant Binding Protein of the Asian Elephant, *Elephas maximus*: Implications for the Role of Lipocalins in Mammalian Olfaction. Biochemistry 2002, 41, 11786-11794.
(11) Pes, D.; Dal Monte, M.; Ganni, M.; Pelosi, P. Isolation of two odorant-binding proteins from mouse nasal tissue. Comp. Biochem. Physiol. 1992, 103B (4), 1011-1017.
(12) Lobel, D.; Jacob, M.; Volkner, M.; Breer, H. Odorant of different chemica classes interact with distinct odorant binding protein subtypes. Chemical senses 2002, 27, 39-44.
(13) Briand, L.; Eloit, C.; Nespoulous, C.; Bezirard, V.; Huet, J.-C.; Henry, C.; Blon, F.; Trotier, D.; Permollet, J.-C. Evidence of an Odorant-Binding Protein in the Human Olfactory Mucus: Location, Structural Characterization, and Odorant-Binding Properties. Biochemistry 2002, 41, 7241-7252.

(14) Pelosi, P. Odorant-Binding Proteins: Structural Aspects. In Annals New York academy of sciences; Olfaction and Taste XII: an international symposium, 1998; pp 281-293.

(15) Spinelli, S.; Ramoni, R.; Grolli, S.; Bonicel, J.; Cambillau, C.; Tegoni, M. The Structure of the Monomeric Porcine Odorant Binding Protein Sheds Light on the Domain Swapping Mechanism. Biochemistry 1998, 37, 7913-7918.

(16) Perduca, M.; Mancia, F.; Del Giorgio, R.; Monaco, H. L. Crystal Structure of a Truncated Form of Porcine Odorant-Binding Protein. Proteins: Structure, Function, and Genetics 2001, 42, 201-209.

(17) Cave, J. W.; Wickiser, J. K.; Mitropoulos, A. N. Progress in the development of olfactory-based bioelectronic chemosensors. Biosensors & bioelectronics 2019, 123, 211-222, DOI: 10.1016/j.bios.2018.08.063.

(18) Pelosi, P.; Mastrogiacomo, R.; Iovinella, I.; Tuccori, E.; Persaud, K. C. Structure and biotechnological applications of odorant-binding proteins. Applied microbiology and biotechnology 2014, 98 (1), 61-70, DOI: 10.1007/s00253-013-5383-y.

(19) Mulla, M. Y.; Tuccori, E.; Magliulo, M.; Lattanzi, G.; Palazzo, G.; Persaud, K.; Torsi, L. Capacitance-modulated transistor detects odorant binding protein chiral interactions. Nature communications 2015, 6, 6010, DOI: 10.1038/ncomms7010.

(20) Paolini, S.; Tanfani, F.; Fini, C.; Bertoli, E.; Pelosi, P. Porcine odorant-binding protein: structural stability and ligand affinities measured by Fourier-transform infrared spectroscopy and fluorescence spectroscopy. Biochimica et biophysica acta 1999, 1431, 179-188.

(21) Sorokowska, A.; Sorokowski, P.; Szmajke, A. Does Personality Smell? Accuracy of Personality Assessments Based on Body Odour. European Journal of Personality 2012, 26 (5), 496-503, DOI: 10.1002/per.848.

(22) Ozeki, C.; Moro, O. A study of the suppression of body odour in elderly subjects by anti-fungal agents. International journal of cosmetic science 2016, 38 (3), 312-8, DOI: 10.1111/ics.12295.

(23) Di Pietrantonio, F.; Cannata, D.; Benetti, M.; Verona, E.; Varriale, A.; Staiano, M.; D'Auria, S. Detection of odorant molecules via surface acoustic wave biosensor array based on odorant-binding proteins. Biosensors & bioelectronics 2013, 41, 328-34, DOI: 10.1016/j.bios.2012.08.046.

(24) Sankaran, S.; Khot, L R.; Panigrahi, S. Biology and applications of olfactory sensing system: A review. Sensors and Actuators B: Chemical 2012, 171-172, 1-17, DOI: 10.1016/j.snb.2012.03.029.

(25) Goncalves, F.; Ribeiro, A.; Silva, C.; Cavaco-Paulo, A. Release of Fragrances from Cotton Functionalized with Carbohydrate-Binding Module Proteins. ACS Appl Mater Interfaces 2019, DOI: 10.1021/acsami.9b08191.

(26) Kozlowski, L. P. IPC—Isoelectric Point Calculator. Biology direct 2016, 11 (1), 55, DOI: 10.1186/s13062-016-0159-9.

(27) Cennamo, N.; Di Giovanni, S.; Varriale, A.; Staiano, M.; Di Pietrantonio, F.; Notargiacomo, A.; Zeni, L.; D'Auria, S. Easy to Use Plastic Optical Fiber-Based Biosensor for Detection of Butanal. PloS one 2015, 10 (3), e0116770, DOI: 10.1371/journal.pone.0116770.

(28) Capo, A.; Pennacchio, A.; Varriale, A.; D'Auria, S.; Staiano, M. The porcine odorant-binding protein as molecular probe for benzene detection. PloS one 2018, 13 (9), e0202630, DOI: 10.1371/journal.pone.0202630.

(29) Vincent, F.; Ramoni, R.; Spinelli, S.; Grolli, S.; Tegoni, M.; Cambillau, C. Crystal structures of bovine odorant-binding protein in complex with odorant molecules. European journal of biochemistry 2004, 271 (19), 3832-42, DOI: 10.1111/j.1432-1033.2004.04315.x.

(30) Goncalves, F.; Castro, T. G.; Nogueira, E.; Pires, R.; Silva, C.; Ribeiro, A.; Cavaco-Paulo, A. OBP fused with cell-penetrating peptides promotes liposomal transduction. Colloids and surfaces. B, Biointerfaces 2018, 161, 645-653, DOI: 10.1016/j.colsurfb.2017.11.026.

(31) Malpeli, G.; Folli, C.; Cavazzini, D.; Sartori, G.; Berti, R. Purification and Fluorescent Titration of Cellular Retinol-Binding Protein. In Methods in Molecular Biology; Redfern, C. P. F., Ed.; 1998; pp 111-122.

(32) Nogueira, E.; Mangialavori, I. C.; Loureiro, A.; Azoia, N. G.; Sárria, M. P.; Nogueira, P.; Freitas, J.; Harmark, J.; Shimanovich, U.; Rollet, A.; Lacroix, G.; Bernardes, G. J. L.; Guebitz, G.; Hebert, H.; Moreira, A.; Carmo, A. M.; Rossi, J. P. F. C.; Gomes, A. C.; Preto, A.; Cavaco-Paulo, A. Peptide anchor for folate-targeted liposomal delivery. Biomacromolecules 2015, 16 (9), 2904-2910, DOI: 10.1021/acs.biomac.5b00823.

(33) Gonçalves, F.; Silva, C.; Ribeiro, A.; Cavaco-Paulo, A. 1-Aminoanthracene Transduction into Liposomes Driven by Odorant-Binding Protein Proximity. ACS Applied Materials & Interfaces 2018, DOI: 10.1021/acsami.8b10158.

(34) Goncalves, F.; Castro, T. G.; Azoia, N. G.; Ribeiro, A.; Silva, C.; Cavaco-Paulo, A. Two Engineered OBPs with opposite temperature-dependent affinities towards 1-aminoanthracene. Scientific reports 2018, 8 (1), 1484, DOI: 10.1038/s41598-018-33085-8.

The term "comprising" whenever used in this document is intended to indicate the presence of stated features, integers, steps, components, but not to preclude the presence or addition of one or more other features, integers, steps, components or groups thereof.

The disclosure should not be seen in any way restricted to the embodiments described and a person with ordinary skill in the art will foresee many possibilities to modifications thereof.

The above described embodiments are combinable.

The following claims further set out particular embodiments of the disclosure.

The invention claimed is:

1. A method of hair care comprising applying a composition comprising an odorant-binding protein comprising an amino acid sequence of any one of SEQ ID NOs: 10-21 to hair of a subject, wherein the odorant-binding protein reduces odor of the hair of the subject.

2. The method of claim 1, the method comprising applying the composition comprising the odorant-binding protein comprising the amino acid sequence of SEQ ID NO: 10.

3. The method of claim 1, the method comprising applying the composition comprising the odorant-binding protein comprising the amino acid sequence of SEQ ID NO: 21.

4. The method of claim 1, the method comprising applying the composition comprising the odorant-binding protein comprising the amino acid sequence selected from any one of SEQ ID NOs: 10-21, wherein the composition is a hair shampoo.

5. The method of claim 1, the method comprising applying the composition comprising the odorant-binding protein comprising the amino acid sequence selected from any one of SEQ ID NOs: 10-21, wherein the protein is present in the composition at 0.1 micromolar to 2 molar.

6. The method of claim 5, the method comprising applying the composition comprising the odorant-binding protein comprising the amino acid sequence selected from any one of SEQ ID NOs: 10-21, wherein the protein is present in the composition at 0.2 micromolar to 1 molar.

7. The method of claim 5, the method comprising applying the composition comprising the odorant-binding protein comprising the amino acid sequence selected from any one of SEQ ID NOs: 10-21, wherein the protein is present in the composition at 0.2 micromolar to 2000 micromolar.

8. The method of claim 1, the method comprising applying the composition comprising the odorant-binding protein comprising the amino acid sequence of SEQ ID NO: 11.

9. The method of claim 1, the method comprising applying the composition comprising the odorant-binding protein comprising the amino acid sequence of SEQ ID NO: 12.

10. The method of claim 1, the method comprising applying the composition comprising the odorant-binding protein comprising the amino acid sequence of SEQ ID NO: 13.

11. The method of claim 1, the method comprising applying the composition comprising the odorant-binding protein comprising the amino acid sequence of SEQ ID NO: 14.

12. The method of claim 1, the method comprising applying the composition comprising the odorant-binding protein comprising the amino acid sequence of SEQ ID NO: 15.

13. The method of claim 1, the method comprising applying the composition comprising the odorant-binding protein comprising the amino acid sequence of SEQ ID NO: 16.

14. The method of claim 1, the method comprising applying the composition comprising the odorant-binding protein comprising the amino acid sequence of SEQ ID NO: 17.

15. The method of claim 1, the method comprising applying the composition comprising the odorant-binding protein comprising the amino acid sequence of SEQ ID NO: 18.

16. The method of claim 1, the method comprising applying the composition comprising the odorant-binding protein comprising the amino acid sequence of SEQ ID NO: 19.

17. The method of claim 1, the method comprising applying the composition comprising the odorant-binding protein comprising the amino acid sequence of SEQ ID NO: 20.

* * * * *